United States Patent
Washizu et al.

(10) Patent No.: US 11,793,659 B2
(45) Date of Patent: Oct. 24, 2023

(54) ORTHOSIS MANUFACTURING SYSTEM, SYSTEM FOR GENERATING CORRECTION DATA FOR MANUFACTURING ORTHOSIS, AND ORTHOSIS MANUFACTURING METHOD

(71) Applicant: Konica Minolta, Inc., Tokyo (JP)

(72) Inventors: Takashi Washizu, Tokyo (JP);
Yoshikazu Tanaka, Osaka (JP);
Atsushi Takahashi, Tokyo (JP);
Takuya Ishigai, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 531 days.

(21) Appl. No.: 16/631,362

(22) PCT Filed: Jun. 8, 2018

(86) PCT No.: PCT/JP2018/022061
§ 371 (c)(1),
(2) Date: Jan. 15, 2020

(87) PCT Pub. No.: WO2019/026424
PCT Pub. Date: Feb. 7, 2019

(65) Prior Publication Data
US 2020/0214870 A1 Jul. 9, 2020

(30) Foreign Application Priority Data
Jul. 31, 2017 (JP) .................. 2017-147909

(51) Int. Cl.
*A61F 5/01* (2006.01)
*B33Y 10/00* (2015.01)
(Continued)

(52) U.S. Cl.
CPC .......... *A61F 5/0111* (2013.01); *B29C 64/386* (2017.08); *B33Y 10/00* (2014.12);
(Continued)

(58) Field of Classification Search
CPC ....... B29C 64/386; B33Y 10/00; B33Y 30/00; B33Y 40/20; B33Y 50/00
See application file for complete search history.

(56) References Cited

U.S. PATENT DOCUMENTS 9,788,600 B2 * 10/2017 Wawrousek ............ G06F 30/17
2008/0292179 A1 11/2008 Busch
(Continued)

FOREIGN PATENT DOCUMENTS

| JP | 2013530757 A | 8/2013 |
|---|---|---|
| WO | 2011163410 A1 | 12/2011 |

OTHER PUBLICATIONS

CNIPA, Notice of the Reasons for Rejection for the corresponding Chinese Patent Application No. 201880050064.9, dated Jul. 27, 2021, with English translation.
(Continued)

*Primary Examiner* — Nahida Sultana
(74) *Attorney, Agent, or Firm* — LUCAS & MERCANTI, LLP (57) ABSTRACT

This orthosis manufacturing system is designed to manufacture an orthosis to be fitted on a human body and provided with: an orthosis modeling data generation unit (2) for generating orthosis modeling data (D4) for the orthosis on the basis of three-dimensional data (D1) of the human body generated by measuring the shape of a portion of the human body to which the orthosis is to be fitted, a model shape data (D2) for the orthosis, and manufacture history data (D3) relating to other orthoses manufactured in the past;
(Continued)

and an orthosis formation unit (3) for three-dimensionally forming the orthosis on the basis of the modeling data (D4).

20 Claims, 10 Drawing Sheets

(51) Int. Cl.
*B33Y 30/00* (2015.01)
*B33Y 50/00* (2015.01)
*B33Y 80/00* (2015.01)
*B29C 64/386* (2017.01)
*G16H 20/30* (2018.01)
*G16H 40/40* (2018.01)
*B33Y 40/20* (2020.01)
*G06T 7/00* (2017.01)
*G06T 7/60* (2017.01)
*G06T 19/20* (2011.01)
*B29L 31/00* (2006.01)

(52) U.S. Cl.
CPC ............... *B33Y 30/00* (2014.12); *B33Y 40/20* (2020.01); *B33Y 50/00* (2014.12); *B33Y 80/00* (2014.12); *G06T 7/0014* (2013.01); *G06T 7/60* (2013.01); *G06T 19/20* (2013.01); *G16H 20/30* (2018.01); *G16H 40/40* (2018.01); *B29L 2031/753* (2013.01); *G06T 2207/10012* (2013.01); *G06T 2207/30196* (2013.01); *G06T 2210/41* (2013.01); *G06T 2219/2021* (2013.01)

(56) References Cited

U.S. PATENT DOCUMENTS

| | | |
|---|---|---|
| 2015/0032242 A1 | 1/2015 | Schouwenburg et al. |
| 2015/0165690 A1 | 6/2015 | Tow |
| 2020/0238626 A1* | 7/2020 | Bleicher .................... A61F 5/14 |
| 2020/0329815 A1* | 10/2020 | Schmid ................... B33Y 10/00 |
| 2021/0069984 A1* | 3/2021 | Opitz ......................... A61F 2/66 |
| 2021/0112920 A1* | 4/2021 | Dinshaw ................ B33Y 80/00 |
| 2021/0161253 A1* | 6/2021 | Irarrázaval .............. G06F 30/20 |
| 2021/0322200 A1* | 10/2021 | Goodnough ........ A61F 5/05891 |
| 2022/0206460 A1* | 6/2022 | Kozu ...................... G06Q 50/04 |
| 2022/0225738 A1* | 7/2022 | Hatano .............. A43B 23/0255 |

OTHER PUBLICATIONS

Extended European Search Report for the corresponding European Patent Application No. 18841282.9, dated Aug. 27, 2020.

International Search Report dated Aug. 21, 2018 for PCT/JP2018/022061 and English translation.

EPO, Partial Supplementary European Search Report for the corresponding European Patent Application No. 18841282.9, dated May 26, 2020.

Office Action dated Aug. 26, 2022 for the corresponding European Patent Application No. 18841282.9.

Office Action dated Aug. 30, 2023, for the corresponding European Patent Application No. 18841282.9.

* cited by examiner

| ORTHOSIS ID NO. | POST-PROCESSING DATA | THREE-DIMENSIONAL SHAPE DATA | MOLDING SHAPE DATA (BEFORE CORRECTION) | MOLDING SHAPE DATA (AFTER CORRECTION) | ORTHOTIST INFORMATION | ORTHOSIS USER INFORMATION | PROCESSING FREQUENCY INFORMATION | REFERENCE FREQUENCY INFORMATION |
|---|---|---|---|---|---|---|---|---|
| A | ... | ... | ... | ... | ... | ... | ... | ... |
| B | ... | ... | ... | ... | ... | ... | ... | ... |
| C | ... | ... | ... | ... | ... | ... | ... | ... |

Columns under FABRICATION HISTORY DATA D3: POST-PROCESSING DATA, THREE-DIMENSIONAL SHAPE DATA, MOLDING SHAPE DATA (BEFORE CORRECTION), MOLDING SHAPE DATA (AFTER CORRECTION)

ORTHOSIS MANUFACTURING SYSTEM, SYSTEM FOR GENERATING CORRECTION DATA FOR MANUFACTURING ORTHOSIS, AND ORTHOSIS MANUFACTURING METHOD

CROSS REFERENCE TO RELATED APPLICATION

This Application is a 371 of PCT/JP2018/022061 filed on Jun. 8, 2018 which, in turn, claimed the priority of Japanese Patent Application No. 2017-147909 filed on Jul. 31, 2017, both applications are incorporated herein by reference.

TECHNICAL FIELD

The present disclosure relates to an orthosis fabrication system, a correction data creation system for orthosis fabrication, and an orthosis fabrication method.

BACKGROUND ART

An "orthosis" to be worn on a part of a human body for correcting, supporting, or fixing the part of the human body has been known. When a function of a part of a human body is lowered mainly by a disease or an injury, an orthosis is worn to limit the movement of a joint of the human body to thereby compensate the function or to protect and support the affected part.

Such a type of an orthosis is generally fabricated to be fitted to the shape of the part of the human body (for example, foot, elbow, wrist, leg, or knee) on which the orthosis is to be worn (hereinafter referred to as "orthosis wearing part"). However, such a type of orthosis differs from a cast made of plaster or the like. It is required to allow the orthosis wearing part to freely move to a certain extent while limiting the movement of the joint of the human body.

Accordingly, an orthosis of this type requires a highly adaptable condition with respect to the orthosis wearing part of the patient in the points of shape, elasticity, and the like. Moreover, an orthosis of this type is also required to have wearing comfortability and strength because it is worn on a daily basis.

Meanwhile, an orthosis wearing part of a patient, a physically disabled aspect (for example, fracture aspect) of a patient, or the like differs by each patient. Therefore, finished forms of respective orthoses have large individual differences.

Conventionally, an orthosis is fabricated manually for each patient by a doctor or a professional engineer (hereinafter referred to as an "orthotist or the like"). A conventional example of a specific method of fabricating a foot sole orthosis is a manual process as described below.

1) Wind a protection film on a foot of a patient.
2) Mark a palpation result on the protection film.
3) Create a negative model of a footprint using a cast.
4) Create a positive model of the footprint by pouring plaster into the negative model of the footprint and curing it.
5) Perform processing based on the mark transferred onto the plaster.
6) To the positive model of the footprint, a film (or sheet) of thermoplastic resin is pressed and cured, whereby an orthosis adapted to the footprint is molded.
7) With respect to the orthosis molded as described above, an orthotist or the like performs post-processing (for example, shape adjustment using a heat gun) to be fitted to the patient to thereby create a final orthosis.

On the other hand, along with recent higher accuracy in a measurement apparatus and a three-dimensional molding apparatus, consideration is given on a method of three-dimensionally molding an orthosis using a three-dimensional molding apparatus (for example, see PTL 1).

CITATION LIST

Patent Literature

PTL 1: Japanese Translation of a PCT application Laid-Open No. 2013-530757

SUMMARY OF INVENTION

Technical Problem

However, a manual fabrication method involves a problem that the molding accuracy in the shape or the like of a molded orthosis is low, and a burden for post-processing by an orthotist or the like is large. In addition, there is also a problem that since the processing amount of post-processing is large, a technical difference is likely to be caused between orthotists who perform post-processing, so that wearing comfortability and rehabilitation period may be different between an orthosis fabricated by one orthotist and an orthosis fabricated by another orthotist.

Regarding this point, in the conventional art of PTL 1, a three-dimensional molding apparatus is used to three-dimensionally mold an orthosis. Therefore, it is expected to have an improvement in the molding accuracy to a certain extent and reduction of fabrication time. However, in such a method, an adaptable level of an orthosis to each patient depends on each designer who creates design data. This may cause a problem similar to that described above.

The present disclosure is made in view of the above-described problems. An object of the present disclosure is to provide an orthosis fabrication system, a correction data creation system for orthosis fabrication, and an orthosis fabrication method that enable molding of an orthosis that fits to a patient more suitably in the molding stage.

Solution to Problem

The present disclosure to solve the abovementioned problems mainly provides an orthosis fabrication system for fabricating an orthosis to be worn by a human body, the system comprising:

an orthosis molding data generation section that generates molding shape data of the orthosis on a basis of three-dimensional shape data of the human body created through shape measurement of an orthosis wearing part of the human body, model shape data of the orthosis, and fabrication history data of another orthosis fabricated in past; and an orthosis molding section that three-dimensionally molds the orthosis on a basis of the molding shape data.

Alternatively, in another aspect, there is provided an orthosis fabrication method for fabricating an orthosis to be worn by a human body, the method comprising:

measuring a shape of an orthosis wearing part of the human body, and generating three-dimensional shape data of the human body;

generating molding shape data of the orthosis on a basis of the three-dimensional shape data, model shape data of the orthosis, and fabrication history data of another orthosis fabricated in past;

three-dimensionally molding the orthosis on a basis of the molding shape data; and storing, as the fabrication history data, a processing amount taken when post-processing is performed on the orthosis after three-dimensional molding, in association with the three-dimensional shape data or the molding shape data.

Alternatively, in another aspect, there is provided a correction data creating system for fabricating an orthosis, the system comprising:

an orthosis molding data generation section that generates molding shape data of the orthosis on a basis of three-dimensional shape data of a human body created through shape measurement of an orthosis wearing part of the human body, model shape data of the orthosis, and fabrication history data of another orthosis fabricated in past; and a storage section that stores data as the fabrication history data, a processing amount taken when post-processing is performed on the orthosis after three-dimensional molding, or a correction amount corrected for a difference between pre-correction molding shape data and the molding shape data, in association with at least one of the three-dimensional shape data and the molding shape data.

Advantageous Effects of Invention

According to the orthosis fabrication system of the present disclosure, an orthosis that fits to a patient more suitably can be molded in the molding stage.

DESCRIPTION OF EMBODIMENTS

A preferred embodiment of the present disclosure will be described below in detail with reference to the accompanying drawings. Note that in the description and the drawings, constituent elements having substantially the same function are denoted by the same reference signs, and repeated description is omitted.

[Overall Configuration of Orthosis Fabrication System]

Figure 1:
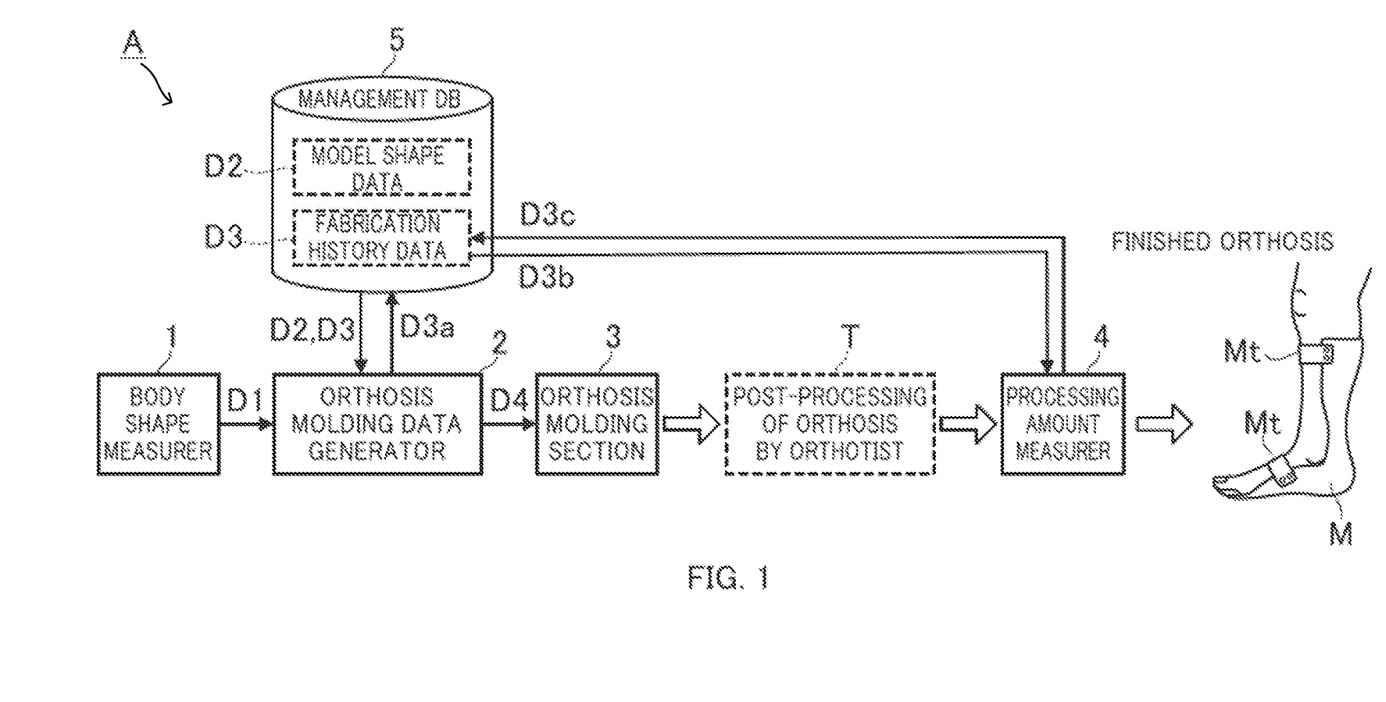
FIG. 1 illustrates an example of an overall configuration of an orthosis fabrication system according to an embodiment.

FIG. 1 illustrates an example of the overall configuration of orthosis fabrication system A according to the present embodiment.

Orthosis fabrication system A according to the present embodiment includes body shape measurement section 1, orthosis molding data generation section 2, orthosis molding section 3, processing amount measurement section 4, and management DB 5.

Body shape measurement section 1 measures the shape of an orthosis wearing part of a human body using a measurement apparatus, and generates three-dimensional shape data D1 of the human body.

Orthosis molding data generation section 2 generates molding shape data D4 of an orthosis on the basis of three-dimensional shape data D1 of the human body, model shape data D2 of the orthosis, and fabrication history data D3 of other orthoses fabricated in the past.

Orthosis molding section 3 uses a three-dimensional molding apparatus to three-dimensionally mold an orthosis on the basis of molding shape data D4.

Processing amount measurement section 4 measures the processing amount in a three-dimensional shape of an orthosis on which post-processing was performed, and stores the processing amount in management DB 5.

Management DB 5 (corresponding to a "storage section" of the present invention) stores fabrication history data D3 of orthoses fabricated in the past. Management DB 5 acquires data related to the processing amount from processing amount measurement section 4, and stores it as fabrication history data D3 in association with three-dimensional shape data D1 or molding shape data D4 of the orthosis.

Note that each of body shape measurement section 1, orthosis molding data generation section 2, orthosis molding section 3, processing amount measurement section 4, and management DB 5 is a computer configured to include, for example, a central processing unit (CPU), a read only memory (ROM), a random access memory (RAM), an input port, and an output port. Respective functions of body shape measurement section 1, orthosis molding data generation section 2, orthosis molding section 3, and processing amount measurement section 4 are realized, for example, by referring to a control program or various types of data stored in the ROM, RAM, and the like by the CPU.

In FIG. 1, a reference sign D1 denotes three-dimensional shape data of a human body, a reference sign D2 denotes model shape data of an orthosis, a reference sign D3 denotes fabrication history data of an orthosis fabricated in the past, and a reference sign D4 denotes molding shape data of an orthosis. Further, reference signs D3a to D3c denote fabrication history data of orthosis M to be fabricated this time. In more detail, the reference sign D3a denotes molding shape data or the like to be newly added to management DB 5, the reference sign D3b denotes molding shape data to be transmitted to processing amount measurement section 4, and the reference sign D3c denotes post-processing data to be acquired from processing amount measurement section 4.

In FIG. 1, arrows indicate a fabrication flow in the case of fabricating orthosis M. Note that the fabrication flow of orthosis fabrication system A according to the present embodiment is configured to incorporate a step of performing post-processing of an orthosis by an orthotist or the like (indicated by a reference sign T in FIG. 1) in the steps performed by the respective sections.

As a fabrication flow in the case of fabricating orthosis M, a process of measuring the shape of an orthosis wearing part of a human body by body shape measurement section 1, a process of generating molding shape data of an orthosis by orthosis molding data generation section 2, a process of molding the orthosis by orthosis molding section 3, a post-processing process of the orthosis by the orthotist or the like, a processing amount measurement process by processing amount measurement section 4, and a processing amount storing process by management DB 5, are performed sequentially.

By such a fabrication flow, one orthosis M is completely fabricated, and fabrication history data D3 of orthosis M is accumulated.

In the present embodiment, an aspect that orthosis M is integrally formed of one material (for example, thermoplastic resin) is shown. However, the configuration of orthosis M can be modified in various manners.

For example, orthosis M may be fabricated by connecting a plurality of parts. Orthosis M is not necessarily formed of uniform one material. Orthosis M may be configured such that components or the like of the material vary depending on the part of orthosis M. Orthosis M may have a pad or the like for flexibility of a protruding portion of a bone. Orthosis M may have a hole in a predetermined area in order to enhance air permeability and flexibility.

As a material constituting orthosis M, it is more preferable to use thermoplastic resin. As thermoplastic resin, for example, polypropylene resin, polyethylene resin, polyvinyl chloride resin, polycarbonate resin, ABS resin, polyamide resin (particularly, nylon 6, nylon 11, nylon 12), methacrylic resin, or the like is particularly useful.

Thermoplastic resin is light in weight and has high strength, and also has high biocompatibility. By using thermoplastic resin, it is possible to realize three-dimensional molding of powder sintered lamination type.

However, as a material constituting orthosis M, UV-curing resin or thermosetting resin may be used instead of the thermoplastic resin. As the UV-curing resin or thermosetting resin, for example, polyurethane resin, epoxy resin, silicone resin, acrylic resin, or the like is useful.

Hereinafter, respective configurations of orthosis fabrication system A according to the present embodiment will be described in detail. As an example, an aspect of fabricating foot sole orthosis M will be described below. Note that as band Mt (see finished form in FIG. 1) for fixing foot sole orthosis M to a foot of a patient, a general purpose one is used.

[Body Shape Measurement Section]

Body shape measurement section 1 measures the shape of an orthosis wearing part of a human body using a measurement apparatus, and generates three-dimensional shape data D1 of the human body.

Figure 2:
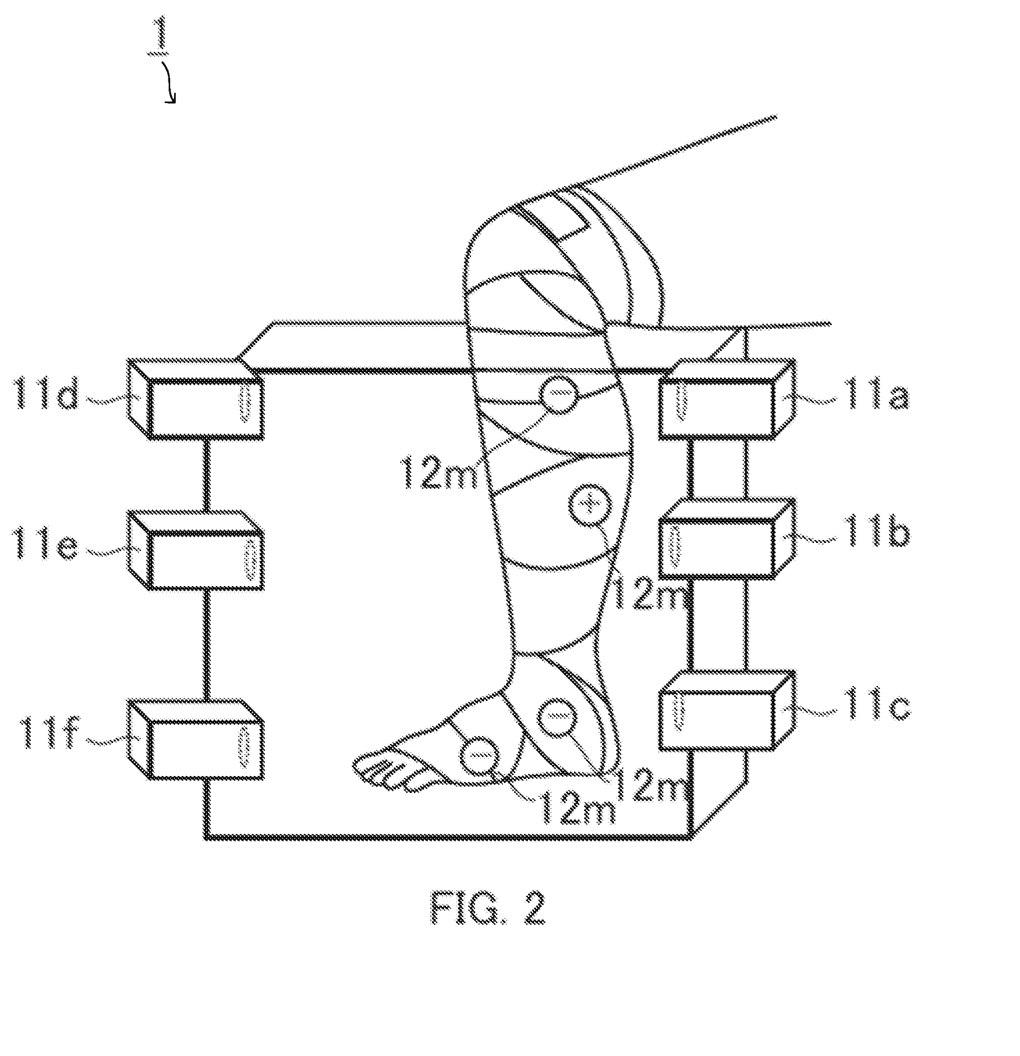
FIG. 2 illustrates an example of a measurement apparatus according to an embodiment.

FIG. 2 illustrates an example of a measurement apparatus.

A measurement apparatus is configured to include a plurality of cameras 11*a* to 11*f* arranged to be able to image a target object from different directions, for example.

Body shape measurement section 1 images an orthosis wearing part of a human body with use of a plurality of cameras 11*a* to 11*f*. Body shape measurement section 1 estimates a three-dimensional shape of the orthosis wearing part in accordance with the principle of triangulation (also referred to as photogrammetry), from a plurality of camera images generated by cameras 11*a* to 11*f*. Note that the method of estimating such a three-dimensional shape is the same as a well-known method. Therefore, the detailed description thereof is omitted herein.

Note that in the case of imaging an orthosis wearing part of a human body, it is more preferable to perform imaging in a state where marks denoted by a reference sign 12*m* in FIG. 2 are applied to the surface of the human body. Thereby, the surface contour of the human body can be clarified, or alignment can be made for connecting camera images.

Note that as a measurement apparatus, body shape measurement section 1 may use a 3D scanner or the like, instead of a plurality of cameras 11*a* to 11*f*.

[Orthosis Molding Data Generation Section]

Orthosis molding data generation section 2 generates molding shape data D4 of orthosis M on the basis of three-dimensional shape data D1 of the human body, model shape data D2 of the orthosis, and fabrication history data D3 of other orthoses fabricated in the past.

Figure 3:
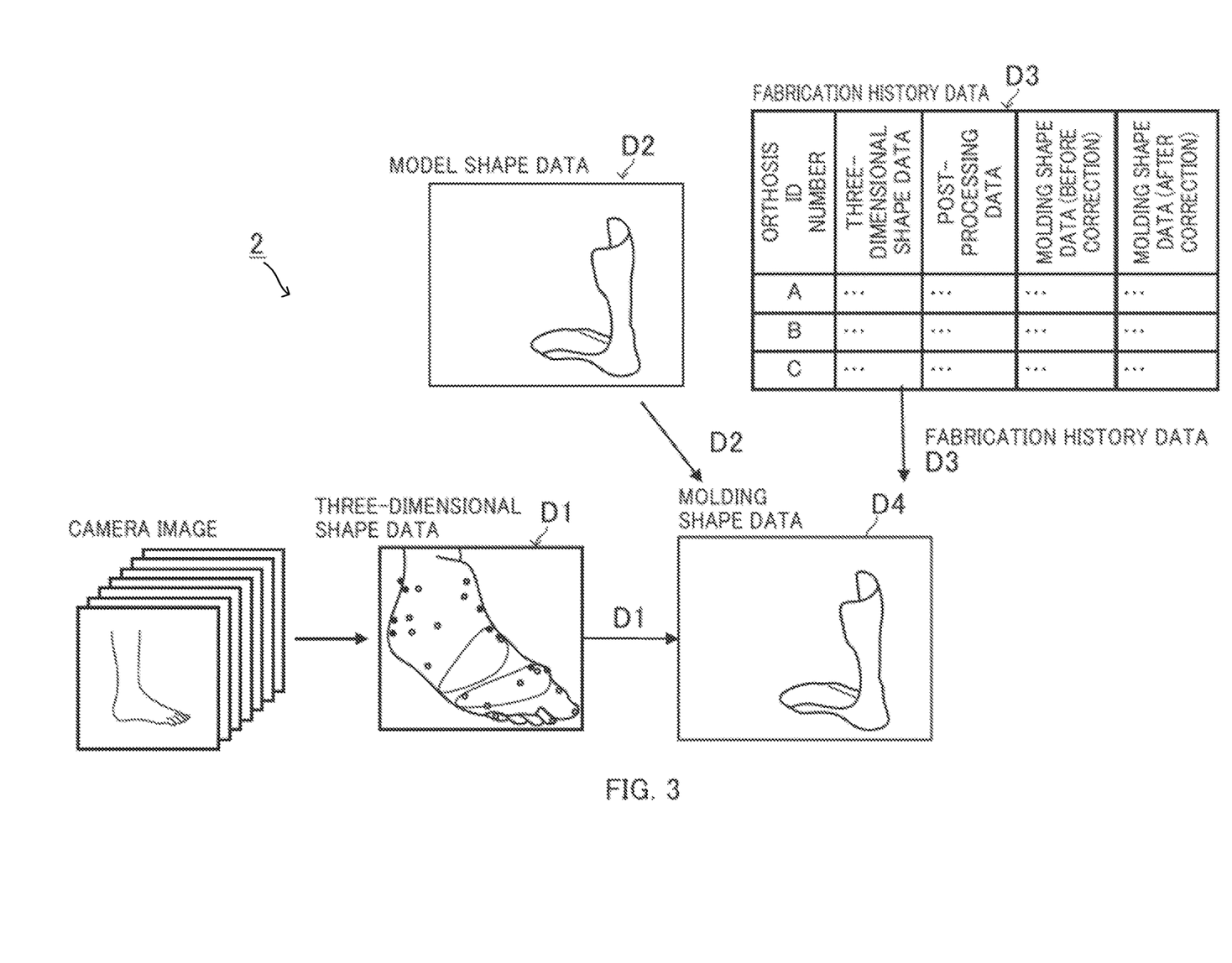
FIG. 3 illustrates exemplary data referred to by an orthosis molding data generation section according to an embodiment.

FIG. 3 illustrates exemplary data referred to by orthosis molding data generation section 2.

"Model shape data D2" is data that defines the base shape of orthosis M. Model shape data D2 defines the thickness and the shape of the material constituting the orthosis for each area (for example, a bone protruding area of a foot, a root area of a toe, or the like) of the orthosis wearing part of the human body, on the basis of an average human body, for example. Model shape data D2 is stored in management DB 5, for example.

"Molding shape data D4" is design data (for example, computer-aided design(CAD) data) that defines the shape and the thickness of each part of orthosis M. Molding shape data D4 is generated by orthosis molding data generation section 2. Note that molding shape data D4 is referred to when orthosis molding section 3 three-dimensionally molds orthosis M.

Orthosis molding data generation section 2 applies three-dimensional shape data D1 of the human body of the orthosis wearing target to model shape data D2 to thereby generate molding shape data D4 that matches the orthosis wearing part of the human body. Orthosis molding data generation section 2 uses, for example, publicly-known template matching or the like to recognize the shape of each area of the orthosis wearing part of the human body from three-dimensional shape data D1, and applies the shape of each area of the orthosis wearing part of the human body to model shape data D2 to thereby generate molding shape data D4 of orthosis M.

However, orthosis molding data generation section 2 according to the present embodiment uses fabrication history data D3 of orthosis M fabricated in the past (hereinafter also referred to as "fabricated orthosis Ma") (for example, fabrication history data D3 of fabricated orthosis Ma similar to orthosis M to be fabricated) as reference information to thereby reflect post-processing aspects performed by an orthotist or the like on molding shape data D4.

"Fabrication history data D3" is data of fabrication history according to fabricated orthosis Ma accumulated in management DB 5. Fabrication history data D3 is, for example, stored data in which post-processing data showing the processing amount of post-processing performed on fabricated orthosis Ma to which identification number is assigned to each fabricated orthosis Ma, three-dimensional shape data of a person who wears fabricated orthosis Ma, molding shape data before correction of fabricated orthosis Ma (also referred to as "pre-correction molding shape data"), molding shape data after correction of fabricated orthosis Ma (correction process will be described below), and the like are associated with each other.

Post-processing data of post-processing in fabrication history data D3 may include, for example, data of processed amount of each area performed on fabricated orthosis Ma (for example, in the case of a sole orthosis, for each of divided areas corresponding to the foot outer side, fibula head, lateral malleolus, fifth metatarsal bone head, fifth toe bone head, foot inner side medial malleolus, navicular bone head, first toe bone, and the like, the deformation amount in the thickness and the deformation amount in the shape), and a difference between shapes before and after post-processing performed on fabricated orthosis Ma.

Figure 4:
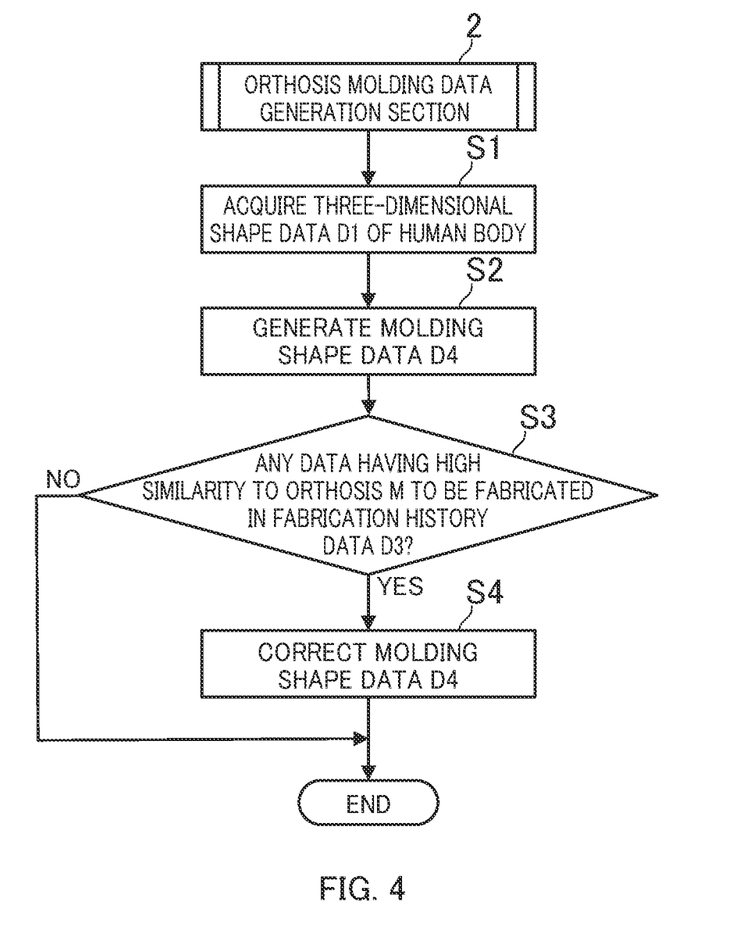
FIG. 4 is a flowchart illustrating an exemplary operation of an orthosis molding data generation section according to an embodiment.

FIG. 4 is a flowchart illustrating an exemplary operation of orthosis molding data generation section 2.

Note that the flowchart of FIG. 4 is a process performed by orthosis molding data generation section 2 in accordance with a computer program, for example.

At step S1, orthosis molding data generation section 2 first acquires three-dimensional shape data D1 of a human body who wears an orthosis from body shape measurement section 1.

At step S2, orthosis molding data generation section 2 acquires model shape data D2 of orthosis M from management DB 5, and, for example, applies three-dimensional shape data D1 of the human body to model shape data D2 to thereby generate molding shape data D4 of orthosis M.

At step S3, orthosis molding data generation section 2 extracts fabrication history data D3 of fabricated orthosis Ma that is similar to orthosis M to be fabricated, from fabrication history data D3 stored in management DB 5. At that time, if there is fabrication history data D3 of fabricated orthosis Ma similar to orthosis M to be fabricated (S3: YES), after acquiring the data, orthosis molding data generation section 2 proceeds to step S4, while if there is no fabrication history data D3 of fabricated orthosis Ma similar to orthosis M to be fabricated (S3: NO), orthosis molding data generation section 2 ends the series of flow.

Note that when extraction is performed with use of the similarity or the like, extraction may be performed using machine learning (deep learning or the like).

At step S3, orthosis molding data generation section 2 compares molding shape data D4 generated at step S2 with molding shape data before correction of fabricated orthosis Ma by, for example, a publicly-known method such as template matching, and extracts fabrication history data D3 of fabricated orthosis Ma having high shape similarity. More preferably, orthosis molding data generation section 2 extracts fabrication history data D3 of fabricated orthosis Ma having the highest similarity.

At step S4, orthosis molding data generation section 2 corrects molding shape data D4 of the fabrication target on the basis of post-processing data in fabrication history data D3 extracted at step S3.

At step S4, orthosis molding data generation section 2 performs addition or subtraction of the processing amount in the post-processing performed on the fabricated orthosis Ma, depending on the shape or thickness of respective areas of molding shape data D4 of the fabrication target (for example, in the case of a foot sole orthosis, parts corresponding to foot outer side, fibula head, lateral malleolus, fifth metatarsal bone head, fifth toe bone head, foot inner side medial malleolus, navicular bone head, first toe bone, and the like of molding shape data D4 of the fabrication target), for example. In particular, in the case of a foot sole orthosis, these are portions that require detailed adjustment for a person who wears the orthosis with no uncomfortable feeling and are adjusted a number of times by an orthotist or the like. Therefore, these are important items for processing. For these reasons, they may also be used as weighting in the case of performing machine learning (deep learning or the like).

Through such processes, molding shape data D4 of a target to be three-dimensionally molded is generated. After generating molding shape data D4, orthosis molding data generation section 2 transmits, to management DB 5, the fabrication history data (three-dimensional shape data D1 of the human body, molding shape data before correction, molding shape data D4 after correction) of orthosis M to be fabricated this time, and stores the data in management DB 5 with an identification number or the like of orthosis M.

Note that the method of extracting fabrication history data D3 by orthosis molding data generation section 2 can be changed in various manners. For example, orthosis molding data generation section 2 may compare with three-dimensional shape data D1 of the human body and extract fabrication history data D3 of an orthosis having high shape similarity. On the other hand, at that time, orthosis molding data generation section 2 may refer to fabrication history data D3 selected arbitrarily by the user.

Further, the method of correcting molding shape data D4 by orthosis molding data generation section 2 can be changed in various manners. For example, orthosis molding data generation section 2 may reflect only information of partial post-processing such as a part similar to orthosis M to be fabricated, of the pre-processing performed on the fabricated orthosis Ma. On the contrary, orthosis molding data generation section 2 may refer to a plurality of pieces of fabrication history data D3, and refer to partial post-processing information from each of the pieces of fabrication history data D3 or use an average value of post-processing information of respective pieces of fabrication history data D3.

Further, the method of reflecting fabrication history data D3 by orthosis molding data generation section 2 can be changed in various manners. For example, it is needless to say that orthosis molding data generation section 2 may constitute a program to generate molding shape data D4 reflecting fabrication history data D3 in one step, on the basis of three-dimensional shape data D1 of the human body, model shape data D2 of orthosis M, and fabrication history data D3 according to similar fabricated orthosis Ma.

[Orthosis Molding Section]

Orthosis molding section 3 uses a three-dimensional molding apparatus to three-dimensionally mold orthosis M on the basis of molding shape data D4.

Figure 5:
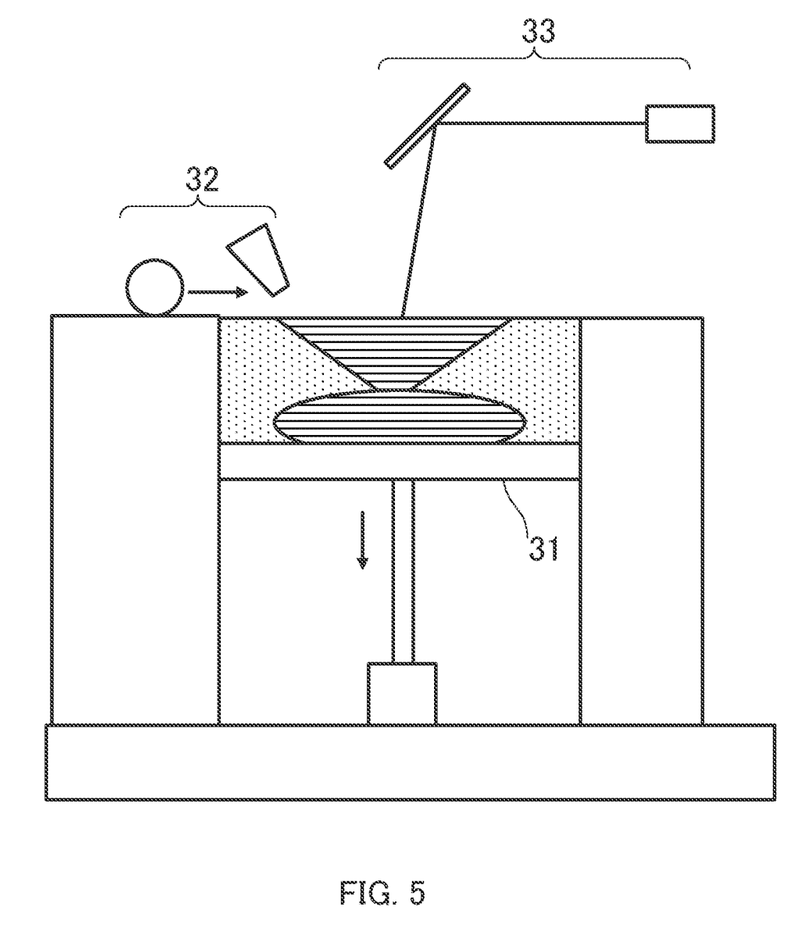
FIG. 5 illustrates an example of a three-dimensional molding apparatus according to an embodiment.

FIG. 5 illustrates an example of a three-dimensional molding apparatus.

The three-dimensional molding apparatus illustrated in FIG. 5 is a three-dimensional molding apparatus of powder sintered lamination type. In the three-dimensional molding apparatus of powder sintered lamination type, three-dimensional molding of thermoplastic resin is relatively easy. In addition, complicated shape can be easily formed. Therefore, it is preferable.

A three-dimensional molding apparatus includes molding stage 31 provided in an opening, powder layer forming section 32 in which a powder layer is formed on molding stage 31, and laser radiation section 33 that irradiate the molding region of the powder layer with a laser beam to sinter or melt and solidify the powder material in the molding region to form a molding layer.

Figure 6:
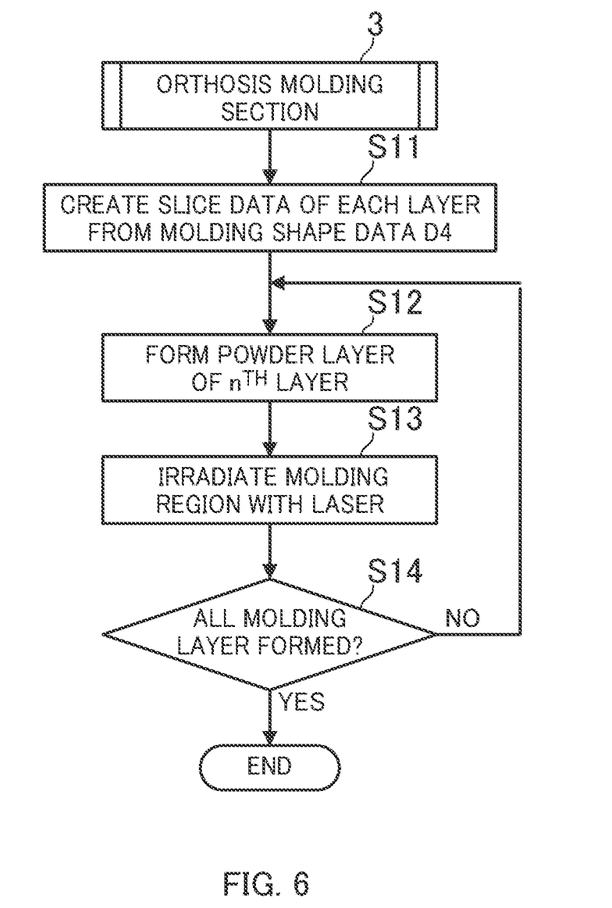
FIG. 6 is a flowchart illustrating an exemplary operation of an orthosis molding section according to an embodiment.

FIG. 6 is a flowchart illustrating an exemplary operation of orthosis molding section 3 according to the present embodiment.

At step S11, orthosis molding section 3 creates slice data for setting a molding region formed in each powder layer from molding shape data D4.

At step S12, orthosis molding section 3 drives powder layer forming section 32 to form an $n^{th}$ powder layer (corresponding to $n^{th}$ layer defined by the slice data) on molding stage 31.

At step S13, orthosis molding section 3 drives laser radiation section 33 to sinter or melt and solidify the powder in the molding region with irradiation of a laser beam to form a molding layer.

At step S14, orthosis molding section 3 determines whether or not the formed molding layer is a final layer. Then, when the formed molding layer is not a final layer (step S14: NO), orthosis molding section 3 lowers molding stage 31 and performs a process of step S12, that is, forming a new powder layer on the molding layer again, and a process of step S13, that is, radiating a laser beam to further form a molding layer. Orthosis molding section 3 repeats such processes to shape a three-dimensional shaped object. Then, when the formed shaping layer is a final layer (step S14: YES), orthosis molding section 3 ends the series of processes in the flowchart.

Through such a flow, orthosis M is molded three-dimensionally.

Note that instead of a three-dimensional molding apparatus of powder-sintered lamination type, orthosis molding section 3 may use a three-dimensional molding apparatus of optical molding type in which liquid resin is irradiated with ultraviolet ray and cured and sequentially laminated, a three-dimensional molding apparatus of ink-jet type in which liquefied material is jetted and sequentially laminated, a three-dimensional molding apparatus of thermal dissolution lamination type in which thermoplastic resin is melted at a high temperature and sequentially laminated, a three-dimensional molding apparatus of sheet laminated type in which sheets are laminated to be shaped, or the like. As a three-dimensional molding apparatus, a cutout method such as cutting processing may be used instead of lamination method.

[Post-Processing by Orthotist or the Like]

Figure 7:
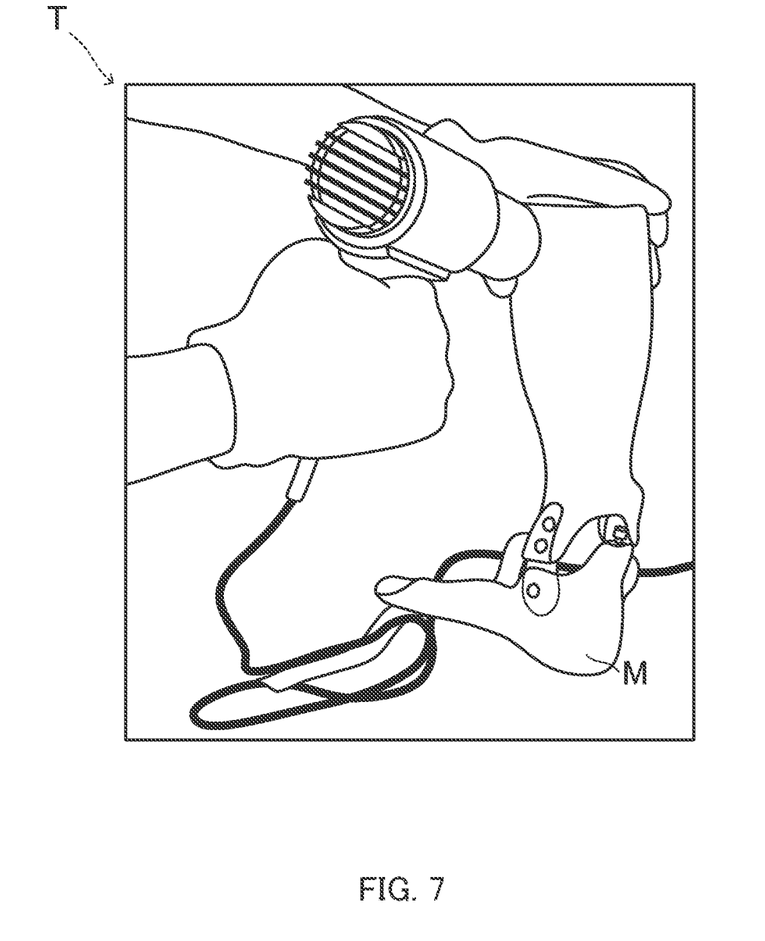
FIG. 7 illustrates an exemplary aspect of post-processing performed on an orthosis by an orthotist or the like according to an embodiment.

FIG. 7 illustrates an exemplary aspect of post-processing performed on orthosis M by an orthotist or the like.

In many cases, orthosis M three-dimensionally molded by orthosis molding section 3 is applied with post-processing by an orthotist or the like for fine adjustment. An orthotist or the like asks a patient to wear orthosis M as a trial, for example, and intuitively performs post-processing on orthosis M on the basis of past experience and knowledge.

As an aspect of post-processing, FIG. 7 illustrates an aspect of performing post-processing of the shape or thickness of orthosis M by an orthotist or the like by plastically deforming orthosis M with use of a heat gun. Note that as an aspect of performing post-processing on orthosis M, an aspect of forming a hole in a predetermined area of orthosis M or spreading a pad member is also acceptable, besides post-processing on shape or thickness of orthosis M.

[Processing Amount Measurement Section 4]

Processing amount measurement section 4 uses a measurement apparatus to measure the processing amount of post-processing performed by an orthotist or the like.

Figure 8:
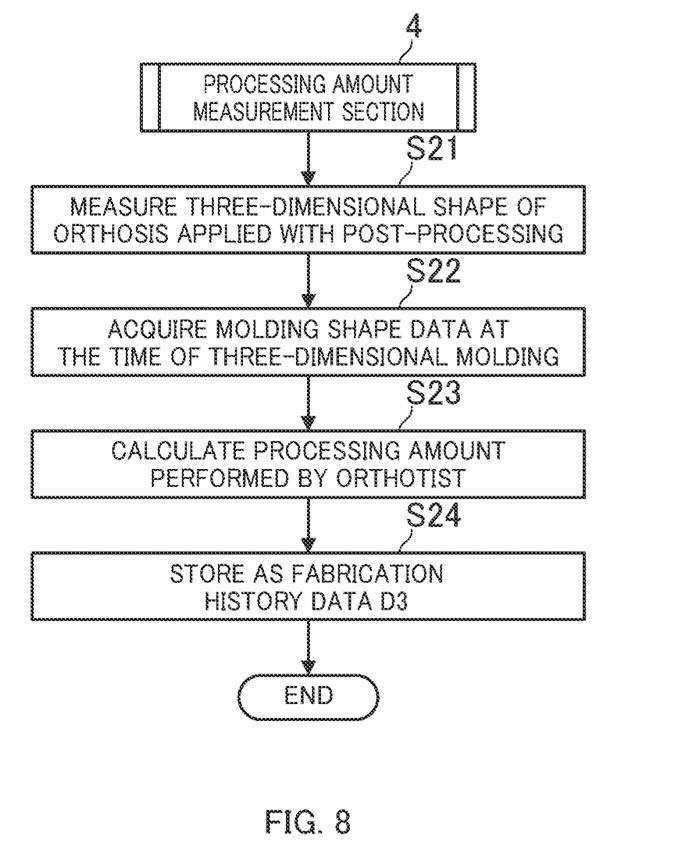
FIG. 8 is a flowchart illustrating an exemplary operation of a processing amount measurement section according to an embodiment.

FIG. 8 is a flowchart illustrating an exemplary operation of processing amount measurement section 4.

At step S21, processing amount measurement section 4 uses a measurement apparatus to measure the three-dimensional shape of orthosis M on which post-processing was performed. Note that the measurement apparatus used by processing amount measurement section 4 may be a plurality of cameras 11a to 11f described with reference to FIG. 2, or another measurement apparatus that can measure the three-dimensional shape.

At step S22, processing amount measurement section 4 acquires shape data of orthosis M before post-processing (here, molding shape data D3b after correction stored in fabrication history data D3) from management DB 5, on the basis of the identification number or the like of orthosis M, for example.

At step S23, processing amount measurement section 4 calculates the processing amount of each area in the post-processing by subtracting the data of the three-dimensional shape of orthosis M before the post-processing from the data of the three-dimensional shape of orthosis M after the post-processing.

At step S24, processing amount measurement section 4 transmits data D3c of the processing amount to management DB 5 along with the identification number of orthosis M, and stores it in management DB 5 as fabrication history data D3.

As described above, orthosis fabrication system A of the present embodiment can sequentially accumulate the history of the processing amount taken when post-processing is performed on orthosis M by the orthotist or the like, as fabrication history data D3.

Therefore, according to orthosis fabrication system A of the present embodiment, when fabricating orthosis M for a patient, it is possible to generate molding shape data D4 on the basis of fabrication history data D3 of fabricated orthosis Ma so as to reflect the aspect of post-processing performed on fabricated orthosis Ma in advance. In orthosis fabrication system A of the present embodiment, for example, by using fabrication history data D3, when fabricating orthosis M similar to fabricated orthosis Ma, it is possible to correct molding shape data D4 in advance by subtracting the processing amount of the area on which post-processing was performed in fabricated orthosis M, for example.

Thereby, in the stage of molding with use of a three-dimensional molding apparatus, it is possible to mold orthosis M that fits to the patient more suitably. Further, this can make post-processing work performed by an orthotist of the like easier or simpler.

(Modification 1)

It is desirable that various types of data related to orthosis M are stored in management DB 5 in association with fabrication history data D3.

Figure 9:
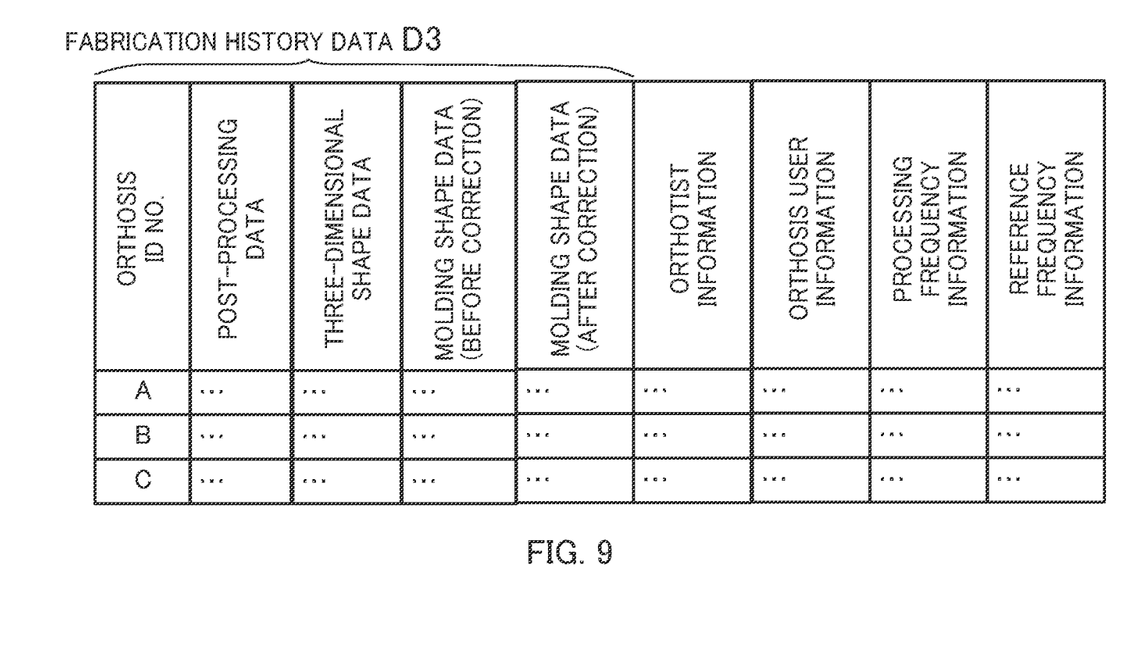
FIG. 9 illustrates exemplary data items stored in a management DB according to Modification 1.

FIG. 9 illustrates exemplary data items stored in management DB 5.

In FIG. 9, for each orthosis, orthotist information, orthosis user information, processing frequency information, and reference frequency information are stored in association with fabrication history data D3.

"Orthotist information" is, for example, information of an orthotist who performed post-processing on fabricated orthosis Ma, such as profile of the orthosis. Orthotist information is useful in the case where it is desired to refer to aspects of post-processing performed by a specific orthotist or it is desired to perform a correction process (correction process of orthosis molding data generation section 2) in consideration of tendency of aspects in post-processing performed by a specific orthotist, for example.

"Orthosis user information" is, for example, symptom information or rehabilitation information of a user who is wearing fabricated orthosis Ma. Orthosis user information is useful in the case where it is desired to refer to aspects of post-processing performed on fabricated orthosis Ma that was fabricated for a user having a specific symptom, or where it is desired to refer to aspects of post-processing of fabricated orthosis Ma used by a user who recovered earlier through rehabilitation, for example.

"Processing frequency information" is information relating to frequency of post-processing performed on fabricated orthosis Ma during use of fabricated orthosis Ma, for example. Processing frequency information is useful in the case where it is desired to refer to aspects of post-processing of fabricated orthosis Ma having strength in which the frequency of post-processing is low, for example.

"Reference frequency information" is information relating to the number of times of being referred to in the correction process by orthosis molding data generation section 2, for example. Reference history information is useful in the case of performing data analysis or the like of fabrication history data D3 that is frequently referred to, for example.

As described above, as in orthosis fabrication system A according to Modification 1, by storing various types of data relating to orthosis M in management DB 5, it is possible to three-dimensionally mold orthosis M satisfying a wide variety of needs in the stage of molding.

(Modification 2)

Orthosis molding data generation section 2 may generate molding shape data D4 of orthosis M after correcting three-dimensional shape data D1 of the human body.

Figure 10:
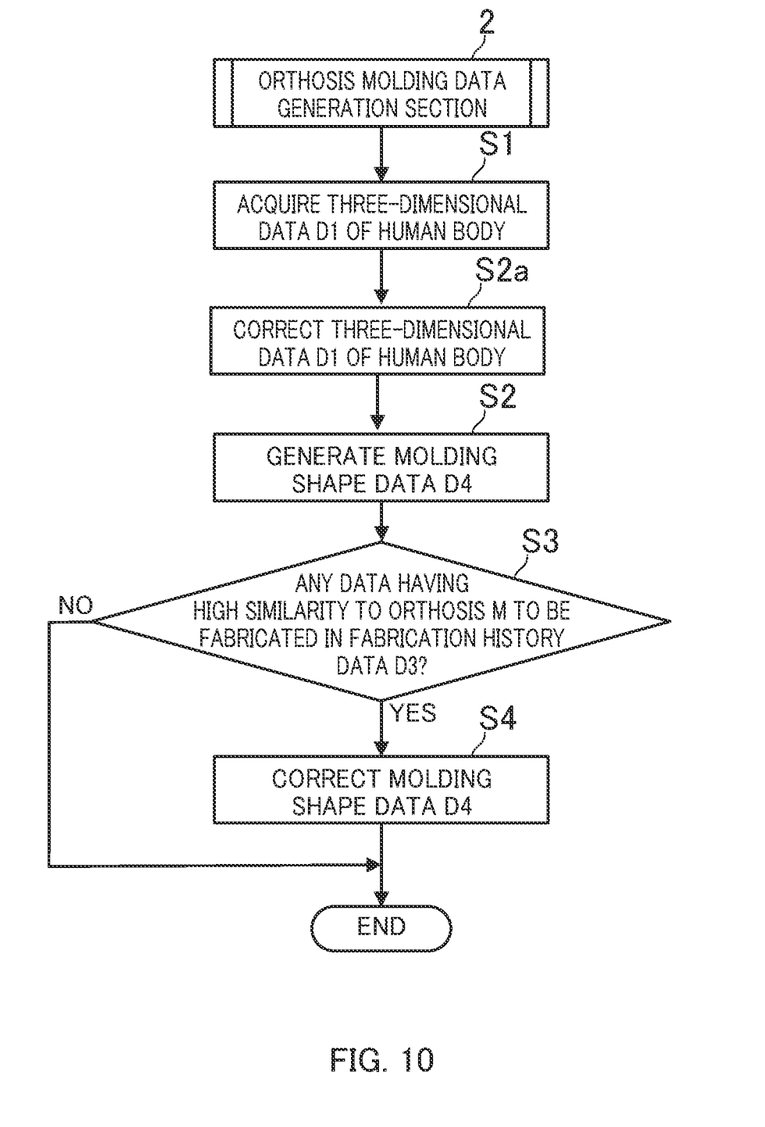
FIG. 10 is a flowchart illustrating an exemplary operation of an orthosis molding data generation section according to Modification 2.

FIG. 10 is a flowchart illustrating an exemplary operation of orthosis molding data generation section 2 according to Modification 2. In the flowchart of FIG. 10, as pre-processing of step S2 in the flowchart of FIG. 4, step S2a of performing correction on three-dimensional shape data D1 is added.

There is a case where the shape of a wearing area of the human body is deformed due to an injury (for example, fracture of the bone) or the like, from the shape in a condition with no injury. Modification 2 addresses such a case. In orthosis molding data generation section 2 according to Modification 2, after correcting measured three-dimensional shape data D1 of the human body into the shape in no injury condition or a shape in a condition to be corrected with use of orthosis M (step S2a), molding shape data D4 of orthosis M is generated on the basis of the shape after the correction (step S2).

Note that the correction process of step S2a may be performed in accordance with a correction rule previously set depending on the position of the injury or the like, or may be performed as appropriate by an operator or the like.

As described above, by enabling three-dimensional shape data D1 of the human body to be corrected as in orthosis fabrication system A according to Modification 2, it is possible to three-dimensionally mold orthosis M having higher accuracy in the molding stage.

Other Embodiments

The present invention is not limited to the embodiments described above. Various modified aspects can be made.

In the embodiments described above, a foot sole orthosis is shown as an example of orthosis M to be fabricated. However, it is needless to say that orthosis fabrication system A according to the embodiments described above is applicable to any other types of orthoses including a coxa orthosis, a long lower limb orthosis, a short lower limb orthosis, a knee orthosis, an orthosis for congenital dislocation of the hip joint, a shoulder orthosis, an elbow orthosis, a long opponency splint, a short opponency splint, a prehension orthosis, a hand dorsiflexion orthosis, an MP extension/flection orthosis, a finger orthosis, and the like.

Further, in the embodiments described above, as an exemplary configuration of orthosis fabrication system A, body shape measurement section 1, orthosis molding data generation section 2, orthosis molding section 3, processing amount measurement section 4, and management DB 5 are realized by different computers, respectively. However, it is needless to say that they can be realized by one computer. Further, programs and data to be read out by those computers and data to be written by those computers may be distributively stored in a plurality of computers.

While specific examples of the present invention have been described above in detail, they are mere examples and do not limit the scope of the appended claims. The technology described in the scope of the appended claims includes various modifications and changes of the specific examples described above as examples.

The present invention is based upon and claims the benefit of priority from Japanese patent application No. 2017-147909, filed on Jul. 31, 2017, the disclosure of which is incorporated herein in its entirety by reference.

INDUSTRIAL APPLICABILITY

According to the orthosis fabrication system of the present disclosure, an orthosis that fits to a patient more suitably can be three-dimensionally molded.

REFERENCE SIGNS LIST 1 body shape measurement section
2 orthosis molding data generation section
3 orthosis molding section
4 processing amount measurement section
5 management DB

The invention claimed is:

1. An orthosis fabrication system for fabricating an orthosis to be worn by a human body, the system comprising:
    a hardware processor that
        generates molding shape data of the orthosis on a basis of three-dimensional shape data of the human body created through shape measurement of an orthosis wearing part of the human body, model shape data of the orthosis, and fabrication history data of another orthosis fabricated in past, and
        three-dimensionally molds the orthosis on a basis of the molding shape data by using a three-dimensional molding apparatus; and
    a processing amount measurer including a measurement apparatus that measures a three-dimensional shape of the orthosis after a post-processing is performed, the processing amount measurer determining a processing amount of the post-processing by determining a difference between the measured three-dimensional shape of the orthosis and the molding shape data, the determined processing amount being stored with the fabrication history.

2. The orthosis fabrication system according to claim 1, wherein
    the fabrication history data is the processing amount taken when post-processing is performed on the orthosis after three-dimensional molding, or a correction amount corrected for a difference between pre-correction molding shape data and the molding shape data.

3. The orthosis fabrication system according to claim 1, further comprising:
a database that stores data as the fabrication history data, the processing amount taken when post-processing is performed on the orthosis after three-dimensional molding, or a correction amount corrected for a difference between pre-correction molding shape data and the molding shape data, in association with at least one of the three-dimensional shape data and the molding shape data.

4. The orthosis fabrication system according to claim 1, wherein
the processing amount of the post-processing stored as the fabrication history data includes a trimming amount of each part of the orthosis.

5. The orthosis fabrication system according to claim 1, wherein
the hardware processor generates pre-correction molding shape data on a basis of the three-dimensional shape data and the model shape data, and
corrects the molding shape data based on the processing amount of the post-processing performed on another orthosis in the fabrication history data, or a correction amount corrected for a difference between the pre-correction molding shape data stored in past and the molding shape data.

6. The orthosis fabrication system according to claim 1, wherein
the hardware processor extracts, from the fabrication history data of the orthosis having a similar shape from among a plurality of pieces of the fabrication history data, the three-dimensional shape data or the molding shape data.

7. The orthosis fabrication system according to claim 1, wherein
the fabrication history data referred to by the hardware processor includes data related to a deformation amount or a thickness amount at a position of foot outer side peroneal bone head, lateral malleolus, fifth metatarsal bone head, fifth toe bone head, foot inner side medial malleolus, navicular bone head, or first toe bone when the post-processing is performed on the orthosis after three-dimensional molding.

8. The orthosis fabrication system according to claim 7, wherein
when extracting the fabrication history data of the orthosis, the hardware processor extracts data by performing machine learning.

9. The orthosis fabrication system according to claim 8, wherein
when performing the machine learning, the hardware processor performs learning by using the deformation amount or the thickness amount as weighting.

10. The orthosis fabrication system according to claim 6, wherein
the hardware processor extracts, from the fabrication history data of a previously fabricated orthosis, at least a part of surface shape or size indicated in the three-dimensional shape data or the molding shape data.

11. The orthosis fabrication system according to claim 1, wherein
the measurement apparatus measures a shape of the orthosis wearing part of the human body by using a 3D scanner or a plurality of cameras.

12. The orthosis fabrication system according to claim 1, wherein
the hardware processor uses a three-dimensional molding apparatus of a powder sintered lamination type to three-dimensionally mold the orthosis.

13. The orthosis fabrication system according to claim 1, wherein
a material of the orthosis includes thermoplastic resin.

14. The orthosis fabrication system according to claim 1, wherein
the orthosis is a foot sole orthosis.

15. The orthosis fabrication system according to claim 3, wherein
the database stores orthotist information of an orthotist who performed the post-processing, in association with the fabrication history data.

16. The orthosis fabrication system according to claim 3, wherein
the database stores user information of a user who is using the orthosis, in association with the fabrication history data.

17. The orthosis fabrication system according to claim 3, wherein
the database stores frequency information of post-processing performed on the orthosis being used, in association with the fabrication history data.

18. The orthosis fabrication system according to claim 3, wherein
the database stores frequency information referred to by the hardware processor, in association with the fabrication history data.

19. An orthosis fabrication method for fabricating an orthosis to be worn by a human body, the method comprising:
measuring a shape of an orthosis wearing part of the human body, and generating three-dimensional shape data of the human body;
generating molding shape data of the orthosis on a basis of the three-dimensional shape data, model shape data of the orthosis, and fabrication history data of another orthosis fabricated in past;
three-dimensionally molding the orthosis on a basis of the molding shape data by using a three-dimensional molding apparatus;
measuring a three-dimensional shape of the orthosis after a post-processing is performed, the processing amount measurer determining a processing amount of the post-processing by determining a difference between the measured three-dimensional shape of the orthosis and the molding shape data; and
storing, as the fabrication history data, the determined processing amount, in association with the three-dimensional shape data or the molding shape data.

20. A correction data creating system for fabricating an orthosis, the system comprising:
a hardware processor that
generates molding shape data of the orthosis on a basis of three-dimensional shape data of a human body created through shape measurement of an orthosis wearing part of the human body, model shape data of the orthosis, and fabrication history data of another orthosis fabricated in past, and
stores, as the fabrication history data, a processing amount taken when post-processing is performed on the orthosis after three-dimensional molding, or a correction amount corrected for a difference between pre-correction molding shape data and the molding shape data, in association with at least one of the three-dimensional shape data and the molding shape data, to a database; and a processing amount measurer including a measurement apparatus that measures a three-dimensional shape of the orthosis after a post-processing is performed, the processing amount measurer determining a processing amount of the post-processing by determining a difference between the measured three-dimensional shape of the orthosis and the molding shape data, the determined processing amount being stored with the fabrication history.

* * * * *